(12) United States Patent
Elliott (10) Patent No.: US 6,902,146 B1
(45) Date of Patent: Jun. 7, 2005

(54) CATHETER VALVE TO PREVENT BLADDER ATROPHY

(76) Inventor: Steven A Elliott, P.O. Box 218, 10700 Main St., Potter Valley, CA (US) 94541

( * ) Notice: Subject to any disclaimer, the term of this patent is extended or adjusted under 35 U.S.C. 154(b) by 0 days.

(21) Appl. No.: 10/436,435

(22) Filed: May 12, 2003

(51) Int. Cl.[7] .............................................. F16K 31/00
(52) U.S. Cl. ...................................... 251/351; 604/246
(58) Field of Search ............................... 604/245, 246, 604/247, 255, 249; 251/351

(56) References Cited

U.S. PATENT DOCUMENTS 85,260 A * 12/1868 Weaver et al. .............. 217/102

* cited by examiner

Primary Examiner—Kevin C. Sirmons
(74) Attorney, Agent, or Firm—Michael I. Kroll (57) ABSTRACT

The present invention 10 discloses an in-line catheter valve having two adjoining sections including a forward assembly 16 having a tube-like structure and a centrally suspended centerpost 40 with the forward assembly pressed and axially connected to and encapsulating the front distal end of an attachment assembly 18 having an extending hollow form having at its respective connecting distal end's face, an aperture 46 receptive of the centerpost 40 while formed at the opposing half of the attachment assembly 18. The radius or diameter of the present invention 10 is reduced by a plurality of stepped progressions to form a radially descending attachment area 30 for the formation of a frictional attachment resulting from the pressing and/or stretching of an elastomeric tube or catheter 12 onto the radially descending attachment area.

9 Claims, 12 Drawing Sheets

ATTACHING THE ELASTOMERIC TUBE OR CATHETER TO THE APPROPRIATE INLET.

INTRODUCING FLUID INTO THE VALVE VIA THE ELASTOMERIC TUBE OR CATHETER.

ADVANCING THE FORWARD ASSEMBLY.

DISLODGING THE CENTERPOST FROM THE APERTURE.

ALLOWING THE EGRESS OF FLUID THERETHROUGH INTO A URINARY OR HUMAN WASTE RECEPTACLE.

FIG. 12

CATHETER VALVE TO PREVENT BLADDER ATROPHY

BACKGROUND OF THE INVENTION

1. Field of the Invention

The present invention relates generally to valves and, more specifically, to an in-line catheter valve that prevents the atrophy of the bladder during convalescence and rehabilitation by allowing it to contract and expand as it does during normal function. Typical catheters known in the art utilize gravity to allow urine to drip into a bag at a constant rate as it is introduced to the entry point of the catheter. During this time the bladder remains dormant as it contains a constant amount of fluid and is prone to atrophy. Furthermore, this method requires the user to wear a catheter bag at all times which can be awkward and embarrassing. The present invention seeks to overcome the aforementioned shortcomings by providing an in-line catheter valve that acts as a petcock to allow the user to maintain normal urinary function during rehabilitation or convalescence. The valve is employed on the distal end of the catheter tube and remains closed to allow the bladder to fill and expand until the valve of the present invention is opened by the user to expel the waste contained therein into a waste receptacle such as a toilet or a urinal or into a catheter bag as needed. The bladder contracts as it is emptied and expands as it fills thereby simulating normal function and allows the user to use regular facilities without the need of changing or emptying collection bags.

The in-line catheter valve of the present invention is primarily composed of two adjoining sections including a forward assembly having a tube like structure and a centrally suspended centerpost, with the forward assembly pressed and axially connected to and encapsulating the front distal end of an attachment assembly having an extending hollow form having at its respective connecting distal end's face, an aperture receptive of the centerpost, while formed at the opposing half of the attachment assembly the radius or diameter of the structure is reduced by a plurality of stepped progressions to form a radially descending attachment area for the formation of a frictional attachment resulting from the pressing and or stretching of an elastomeric tube or catheter onto the radially descending attachment area. The attachment assembly of the present invention is of tubular form having on and radially disposed its exterior surface a plurality of gripping elements to help the user in the gripping and application of rotational torque to the attachment assembly so that the integral thread members placed on the distal end may cause the forward assembly to advance when rotated against a set of correlating thread members present about the point of attachment where the forward assembly and attachment assembly conjoin. During the rotation and advancement of the forward assembly the centerpost becomes dislodged from the aperture present at the attachment assembly effectively unplugging the aperture to allow for the free flow of the fluid held back in the attachment assembly to go through the outlet present at the forward assemblies frontmost distal end. Coating the engaging portion of the centerpost and inner engaging circumference of the aperture a gasket is produced having on one portion a flange or ring the correlates in form and engages an indenture or aperture of similar shape made in the structure of the mating gasket to indicate complete closure and formation of a seal and to produce an area with an increased coefficient of friction to form a seal that is not easily overcome by vibration of rubbing of the present invention against the users body preventing unintentional opening or loosening that may otherwise cause leakage. During the prolonged wearing of a urinary catheter the bladder tends to atrophy from the constant drip drain effect of a collection bag, not allowing the bladder to function in a normal manner. The use of a urinary catheter valve mimics the natural expansion and contraction of the bladder, which will actually shorten the convalescence and rehabilitation of the user wearing a urinary catheter for an extended period of time.

2. Description of the Prior Art

There are other valve devices designed for catheters. Typical of these is U.S. Pat. No. 4,055,179 issued to Manschot, et al. Oct. 25, 1977.

Another patent was issued to Larkin on Aug. 9, 1983 as U.S. Pat. No. 4,397,442. Yet another U.S. Pat. No. 4,895,346 was issued to Steigerwald on Jan. 23, 1990 and still yet another was issued on Feb. 11, 1992 to Denard as U.S. Pat. No. 5,087,252.

Another patent was issued to Levasseur on Jan. 12, 1993 as U.S. Pat. No. 5,178,186. Yet another U.S. Pat. No. 5,322,518 was issued to Schneider et al. on Jun. 21, 1994. Another was issued to Frassica on Feb. 11, 1997 as U.S. Pat. No. 5,601,537 and still yet another was issued on Aug. 22, 2000 to Pfeiderer et al. as U.S. Pat. No. 6,106,503. Another patent was issued to Eshel on Aug. 7, 2001 as U.S. Pat. No. 6,270,053.

A two-piece valve including a first tubular member having a flow passageway therethrough with a tapered valve seat formed at one end of the flow passageway. A second tubular member is provided having a flow passageway therethrough and a valve element mounted in the flow passageway on the axis thereof. The first and second tubular members are slidably telescopically engaged with each other with one end of the first tubular member slidably positioned inside one end of the second tubular member. The valve element of the second tubular member has a tapered valve surface formed thereon adapted to move into and out of sealing engagement with the tapered valve seat of the first tubular member when the tubular members are telescoped axially one inside the other. The taper angles of the valve element and seat are in the "self-holding" category so that when the valve element is firmly seated in the valve seat the parts will be retained in mating engagement without any additional retaining means.

An improved in-line sleeve valve comprises a modular tubular port having a stationary plug concentrically supported therein and a reciprocating tubular sleeve arranged for sealing against the stationary flange. A resilient, flexible flange connects the tubular sleeve and the tubular port. The flange is sufficiently elastic allow easy manual displacement of the sleeve from the tubular stationary plug in order to allow the flow of liquid, but is biased in a first direction so as to return the tubular sleeve to a position abutting the stationary plug upon release thereof.

A valve assembly comprising, a hollow body member having a cavity, a compression member received on one end of the body member and having an annular flange aligned with the cavity, a device for adjusting the position of the compression member relative to the body member, and a valve device for sealingly engaging against a catheter passing through the valve device, and responsive to compression by the compression member to immobilize the catheter in the valve device.

The urinary catheter is insertable into the urinary bladder of a human male through the penis and urethra for the withdrawal of urine from the urinary bladder. The catheter comprises an elongated tubular flexible element having a pair of end portions, with the first end portion constituting the leading and of the catheter which is introduced into the urinary bladder. One or more openings are provided in the first end portion for delivering urine from the urinary bladder into the tubular flexible element. The other end portion of the tubular flexible element constitutes the trailing end of the catheter and is not insertable into the penis. Valve means are provided in the other end portion for opening and closing the tubular element to permit withdrawal of urine from the tubular element or collection of urine within the tubular element. A support strap is provided for the tubular element. The strap has an adhesive surface adapted for securing the strap to the penis for preventing the accidental withdrawal of the tubular element from the penis and urethra.

A valve stem and body combination for flow control in fluid delivery systems for biomedical applications. The valve body includes a smaller conduit that can be aligned with an exit port in the valve stem to achieve a flow-through mode of operation. The flow through the stopcock is controlled by axially turning the valve stem within the valve body, thus making the stopcock streamline in operation. A dead stop combination is provided for assuring an open and closed state of the stopcock. In addition, the valve stem and body can be marked to assist the user in aligning the exit port and smaller conduit.

A valve device for a catheter with a catheter hub. A tubular housing has one end provided with an outer cone for fitting into an inner cone of the catheter hub and has a valve body within acting as a locking member of an axial channel for the passage of an elongate object. The housing is provided with an axially directed protrusion forming a radial space together with the outer surface of the outer cone and has a locking member cooperating with a complementary member at the catheter hub projecting into the space so as to act as a disconnection lock. Thus, a valve device is provided that is suitable for use with a catheter system destined for venous applications according to the Seldinger method, and which ensures catheter.

Apparatus and methodology for applying catheters, dilators and occluders to mammalian genitourinary and gastrointestinal passages, using rotational manipulation of threaded or helically-formed catheters and threaded dilators and occluders. Threaded or helical catheters are inserted into the opening of the selected passage far enough to engage a thread segment; the other end of the catheter is then manually rotated to draw the catheter into the passage. Threaded dilators and occluders are similarly applied.

The invention relates to a catheter valve for permanently or discontinuously draining body cavities and discharging urine. The catheter valve consists of a two-component housing having a cylindrical portion and a conical portion. The conical portion houses a shaft that slides along the longitudinal axis of the housing. At a tip of the conical portion is a urine inlet opening that allows urine or other bodily fluids to flow into the catheter. At an opposite end is a urine outlet opening that allows the fluid to flow out of the catheter. The shaft controls the flow of fluid through the catheter by selectively sealing the urine outlet opening on the catheter. In addition, a locking mechanism is provided to keep the shaft apart from the outlet valve, thus allowing free flow of fluid through the catheter.

A catheter valve including a housing engaging at least a portion of a tubular member is provided. The tubular member having distal and proximal open ends defining a flow-through passage therebetween, the tubular member further having a proximal portion of a deformable and therefore twistable structure and a distal portion of a more rigid structure, the proximal portion being partially and circumferentially attached to an inner surface of the housing, wherein dimensions of the housing of the proximal portion and of the distal portion are selected such that when the distal portion is rotated, the proximal portion is twisted so as to block passage of fluid through the tubular member and therefore through the catheter valve and the distal portion is secured by the housing so as to prevent self untwisting of the proximal portion.

While these valves may be suitable for the purposes for which they were designed, they would not be as suitable for the purposes of the present invention, as hereinafter described. The in-liner catheter valve of the present invention overcomes the shortcomings of the aforementioned devices of the prior art by allowing the bladder to expand and contract as it does during normal function while allowing the user to selectively release the build-up therein when and where appropriate.

SUMMARY OF THE PRESENT INVENTION

The present invention discloses an in-line catheter valve having two adjoining sections including a forward assembly having a tube-like structure and a centrally suspended centerpost with the forward assembly pressed and axially connected to and encapsulating the front distal end of an attachment assembly having an extending hollow form having at its respective connecting distal end's face, an aperture receptive of the centerpost while formed at the opposing half of the attachment assembly. The radius or diameter of the present invention is reduced by a plurality of stepped progressions to form a radially descending attachment area for the formation of a frictional attachment resulting from the pressing and/or stretching of an elastomeric tube or catheter onto the radially descending attachment area. The attachment assembly of the present invention is of tubular form having radially disposed on its exterior surface a plurality of gripping surfaces to help the user in the gripping and application of rotational torque to the attachment assembly so that the integral thread members placed on the distal end may cause the forward assembly to advance when rotated against a set of correlating thread members present about the point of attachment where the forward assembly and attachment assembly conjoin. During the rotation and advancement of the forward assembly, the centerpost becomes dislodged from the aperture present at the attachment assembly effectively unplugging the aperture to allow for the free flow of the fluid held back in the attachment assembly to go through the outlet present at the forward assemblies frontmost distal end.

A primary object of the present invention is to provide a valve for a catheter that is in-line to the catheter that eliminates the need for a urinary bag and allows the user to relieve themselves as desired.

Another object of the present invention is to provide a urinary catheter valve that will contribute greatly to the health of the bladder during the period of time a urinary catheter is being worn by the patient.

Yet another object of the present invention is to provide a urinary catheter valve that mimics the natural expansion and contraction of the bladder, which will shorten the convalescence and rehabilitation of the user wearing a urinary catheter for an extended period of time by preventing the atrophication of the bladder during such time.

Another object of the present invention is to provide a valve for a catheter having a rotational means for releasing a restrained fluid.

Yet another object of the present invention is to provide a valve for a catheter having a centerpost with a corresponding aperture that may be displaced in and out of the aperture by means of displacement of a forward assembly about a set of integral screw threads for the selective sealing and opening of the aperture when rotated.

Still yet another object of the present invention is to provide a valve for a catheter having a radially descending attachment area for the frictional attachment of an elastomeric tube thereover.

Another object of the present invention is to provide a valve for a catheter having radially surrounding gripping elements surrounding the outside of the forward assembly.

Yet another object of the present invention is to provide a valve for a catheter having a centerpost and aperture with correlating gaskets with one gasket having a flange or ring that engages an indentation or aperture in the respective gasket to form a confirming and vibration or accident proof seal.

Still yet another object of the present invention is to provide a valve for a catheter having a spout that releases fluid therethrough in a directable stream.

Additional objects of the present invention will appear as the description proceeds.

The present invention overcomes the shortcomings of the prior art by providing an in-line valve for a catheter having a forward assembly with an integral streaming spout having gripping elements radially surrounding the outside portion while supporting a centerpost having a gasket used to seal an aperture with a relative gasket that forms said seal more adequately, that may be opened and closed by rotating said forward assembly about the attaching elements screw members with said attachment assembly having a radially descending attachment area used for the attachment there at and over, of a tube or catheter to provide for the user a system of relieving themselves regularly without the need of a urinary bag. The present invention serves to replicate the natural expansion and contraction of the bladder during convalescence and rehabilitation thereby preventing the atrophication of the bladder.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

With regard to reference numerals used, the allowing numbering is used throughout the drawings.

10 present invention
12 catheter
14 receptacle
16 forward assembly
18 attachment assembly
20 dust cap
22 flange
24 gripping surface
26 inlet
28 outlet
30 descending attachment flanges
32 fluid
34 conduit
36 centerpost supports
38 O-ring like flange
40 centerpost
42 threads
44 gasket
46 aperture of attachment assembly
48 stop ring
50 flange

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments since practitioners skilled in the art will recognize numerous other embodiments as well. For a definition of the complete scope of the invention, the reader is directed to the appended claims.

Figure 1:
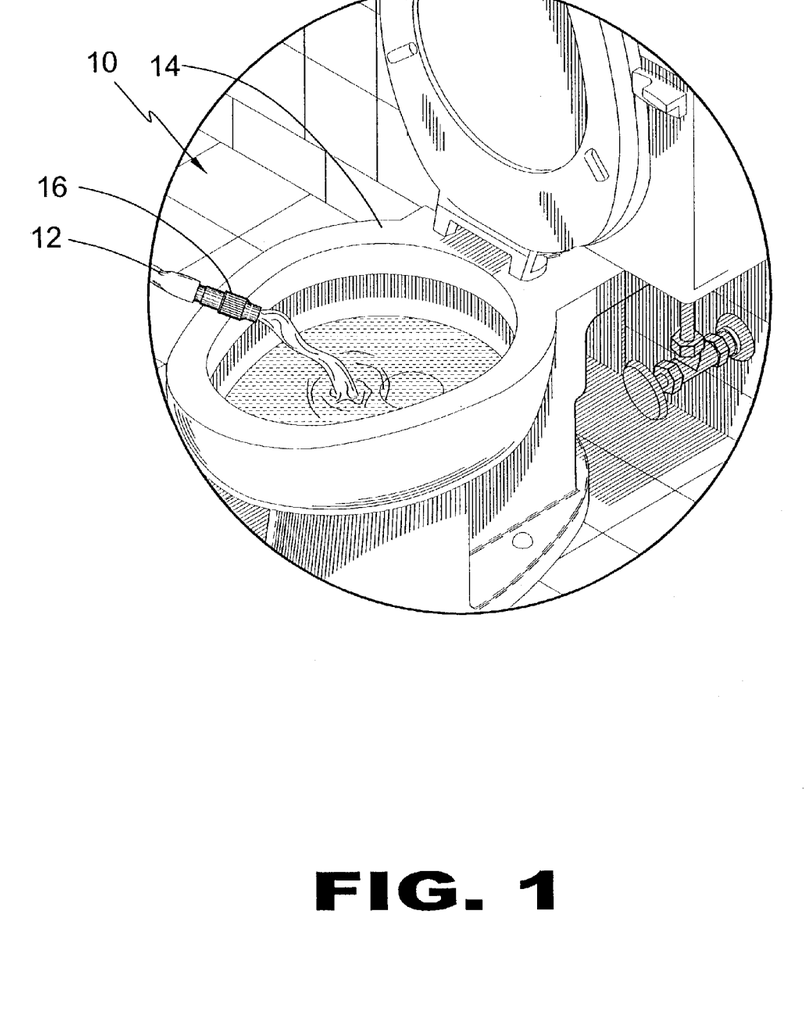
FIG. 1 is an illustrative view of the present invention.

Turning to FIG. 1, shown therein is an illustrative view of the present invention 10. Shown is the present invention 10 comprising a urinary catheter valve connected to a catheter 12 providing means for a user to selectively discharge their bladder without the use of a urine collection bag. The valve is a linearly constructed catheter valve that attaches in line and within a patients catheter having an axially engageable forward assembly 16 that provides a sealing and locking means that allows for the user to relieve themselves regularly at their discretion by simply rotating the forward assembly to break the valve seal and release any urine into a suitable receptacle 14 thereby eliminating the constant need for a urine bag or any other inconvenient urine storage receptacle that are typically associated with urinary catheters.

Figure 2:
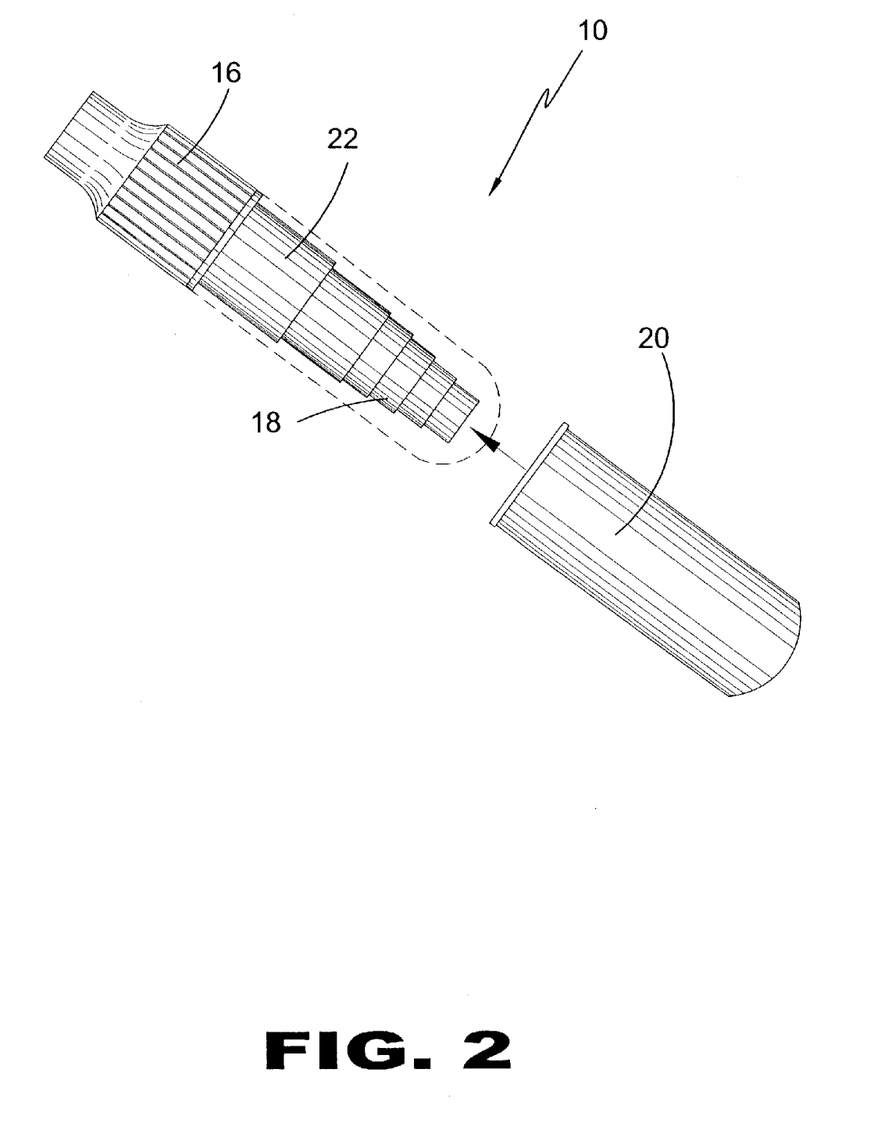
FIG. 2 is a front view of the present invention.

Turning to FIG. 2, shown therein is a front view of the present invention 10. Shown is the present invention 10 having an extending tube like structure having two primary components comprising the forward assembly 16 and attachment assembly 18. The dust cap 20 is pressed onto the distal end of the attachment assembly 18 until the surface of the inner diameter of the dust cap 20 frictionally engages the surface of the outer diameter of the largest flange 22 of the attachment assembly creating an airtight seal.

Figure 3:
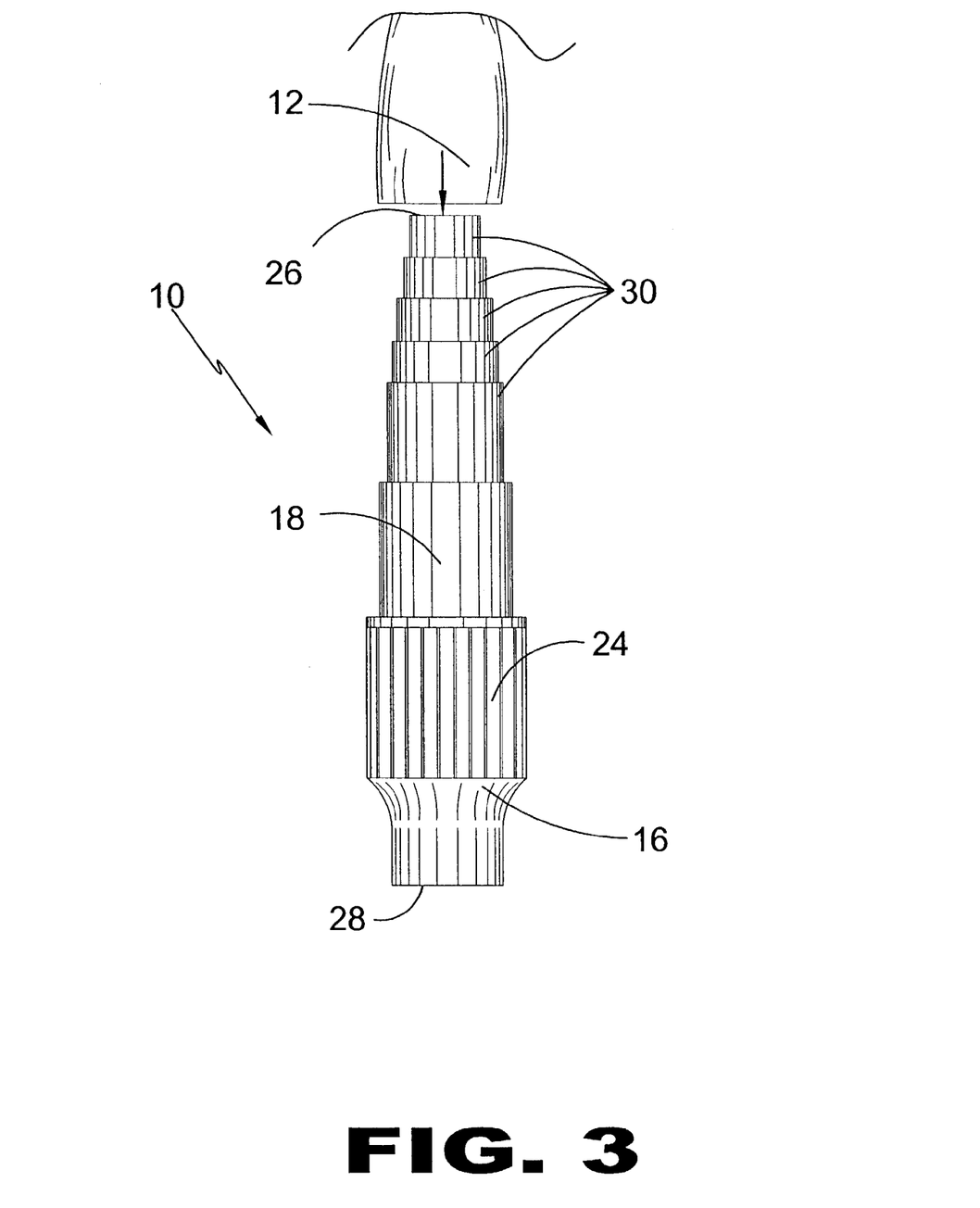
FIG. 3 is a side view of the present invention.

Turning to FIG. 3, shown therein is a side view of the present invention 10. Shown is the present invention 10 having an extending tube-like structure having two primary components comprising the forward assembly 16 and attachment assembly 18. The forward assembly 16 is pressed onto and axially rotatable about the attachment assembly 18 on a set of integral mating screw-like threads placed within the distal end of the forward assembly and the exterior distal end of the attachment assembly to allow for the forward advancement of the forward assembly 16 relative to the attachment assembly 18 when rotation is achieved by an applied rotational torque placed on the knurled exterior gripping surface 24 of the forward assembly. Also shown are an inlet 26, outlet 28, catheter 12, and the radially descending multiple attachment flanges 30 of the attachment assembly 18.

Figure 4:
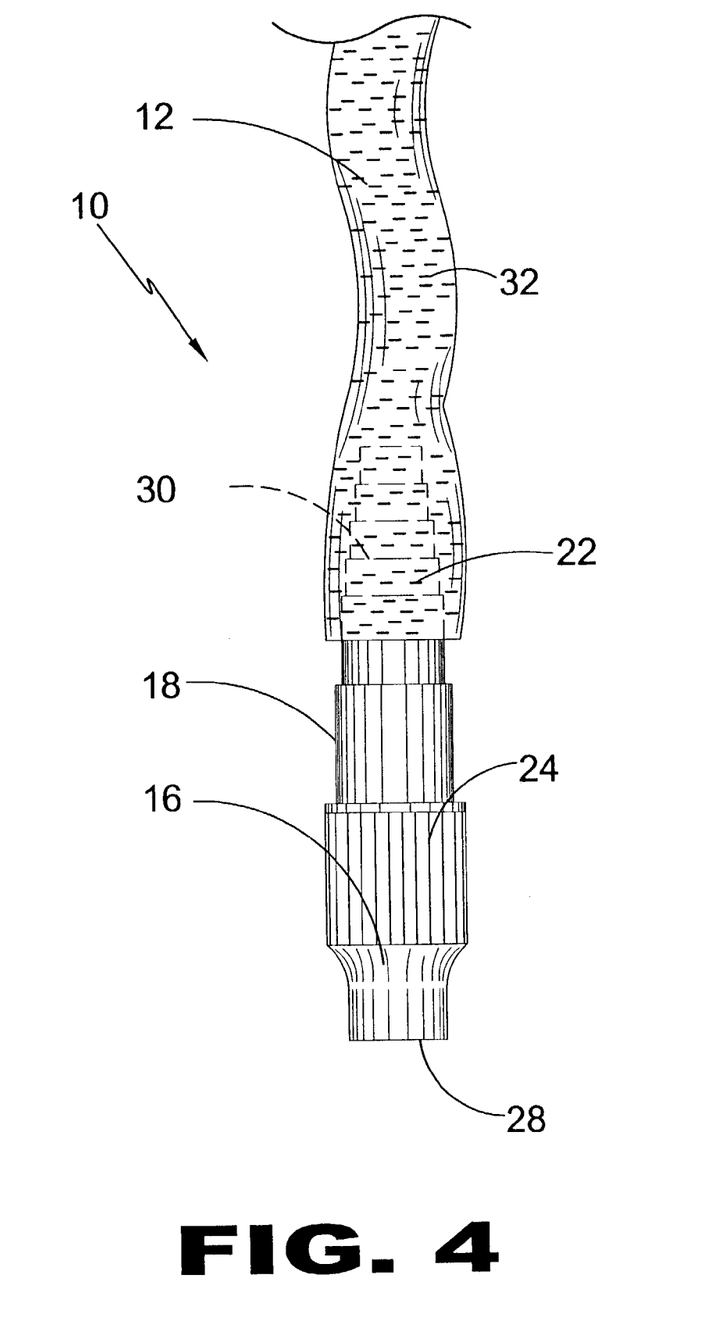
FIG. 4 is a side view of the present invention.

Turning to FIG. 4, shown therein is a side view of the present invention 10. Shown is the present invention 10 having an attachment assembly 18 mounted within a catheter tube 12 having fluid 32 therein until the tube frictionally engages the attachment assembly 18. The radially descending attachment flanges 30 provides multiple incremental surfaces or flanges 22 which provide means for mounting various sized tubes 12 as well as the increasing diameter during the life of the tube. At the other distal end of the attachment assembly 18 is mounted the forward assembly 16 providing means for selectively opening and closing the catheter valve by interaction of mating screw-like threads positioned on the engaging surfaces of the forward assembly 16 and attachment assembly 18. Also shown are outlet 28 and gripping surface 24.

Figure 5:
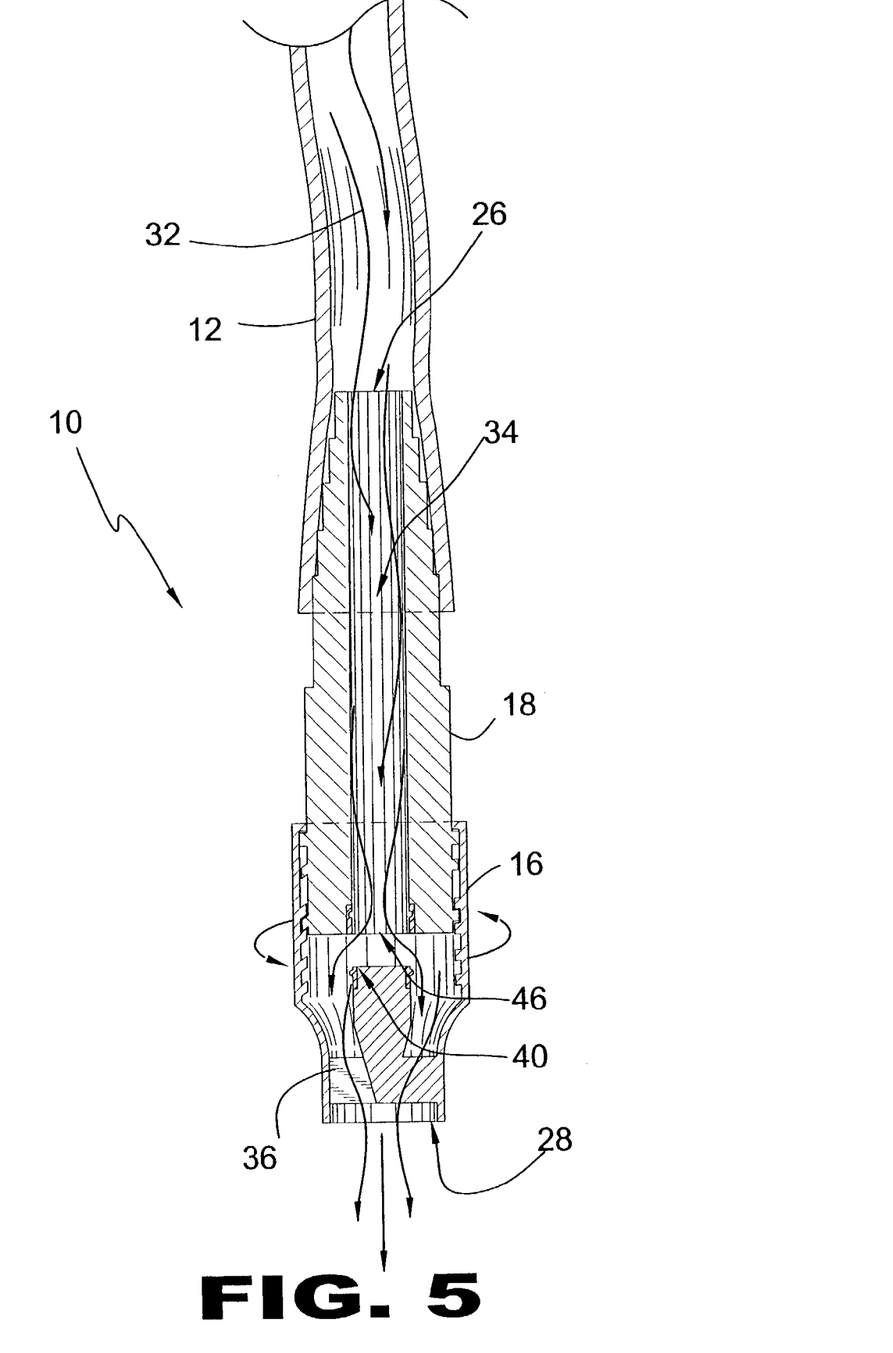
FIG. 5 is a side sectional view of the present invention in use.

Turning to FIG. 5, shown therein is a side sectional view of the present invention 10 in use. Shown is a sectional view depicting the flow of fluid 32 when, the forward advancement of the forward assembly 16 had been applied and brought to a displacement that dislodges the centerpost 40 from the aperture 46 at the distal end of the attachment assembly's 18 cavity 34. Additionally shown is the contained fluid 32 depicted by arrows flowing through the elastomeric catheter tube 12 through the inlet 26 and inner cavity 34 of the attachment assembly 18 out the aperture 46 at the distal end of the cavity 34, around the centerpost 40, past the centerpost supports 36 and finally though the outlet 28 in the form of a divertable stream that may be directed into a proper urinary or human waste receptacle.

Figure 6:
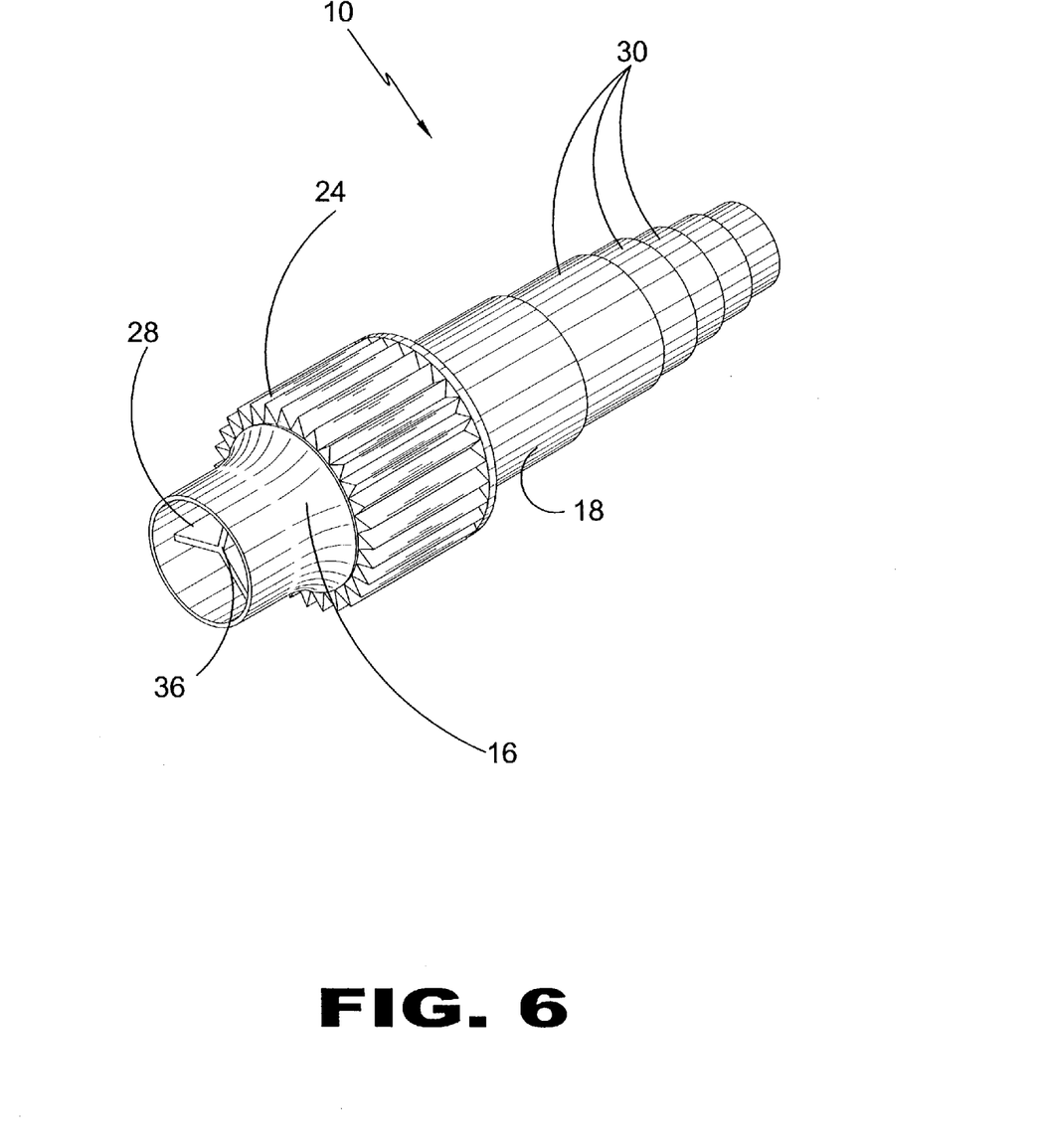
FIG. 6 is a perspective view of the present invention.

Turning to FIG. 6, shown therein is a perspective view of the present invention 10. Shown is the present invention 10 being a catheter valve having an axially rotatable forward assembly 16 having a knurled exterior gripping surface 24 enabling the user to easily open and close the present invention with minimal pressure. The forward assembly 16 is mounted onto an attachment assembly 18 having means for sealing the forward assembly and attachment assembly at one distal end while the other distal end provides a radially descending attachment area 30 that is inserted into the catheter tube. The forward assembly 16 is connected to the attachment assembly 18 that serves as a base for the forward assembly to progressively rotate about mating integral screw-like threads. Also shown are outlet 28 and centerpost supports 36.

Figure 7:
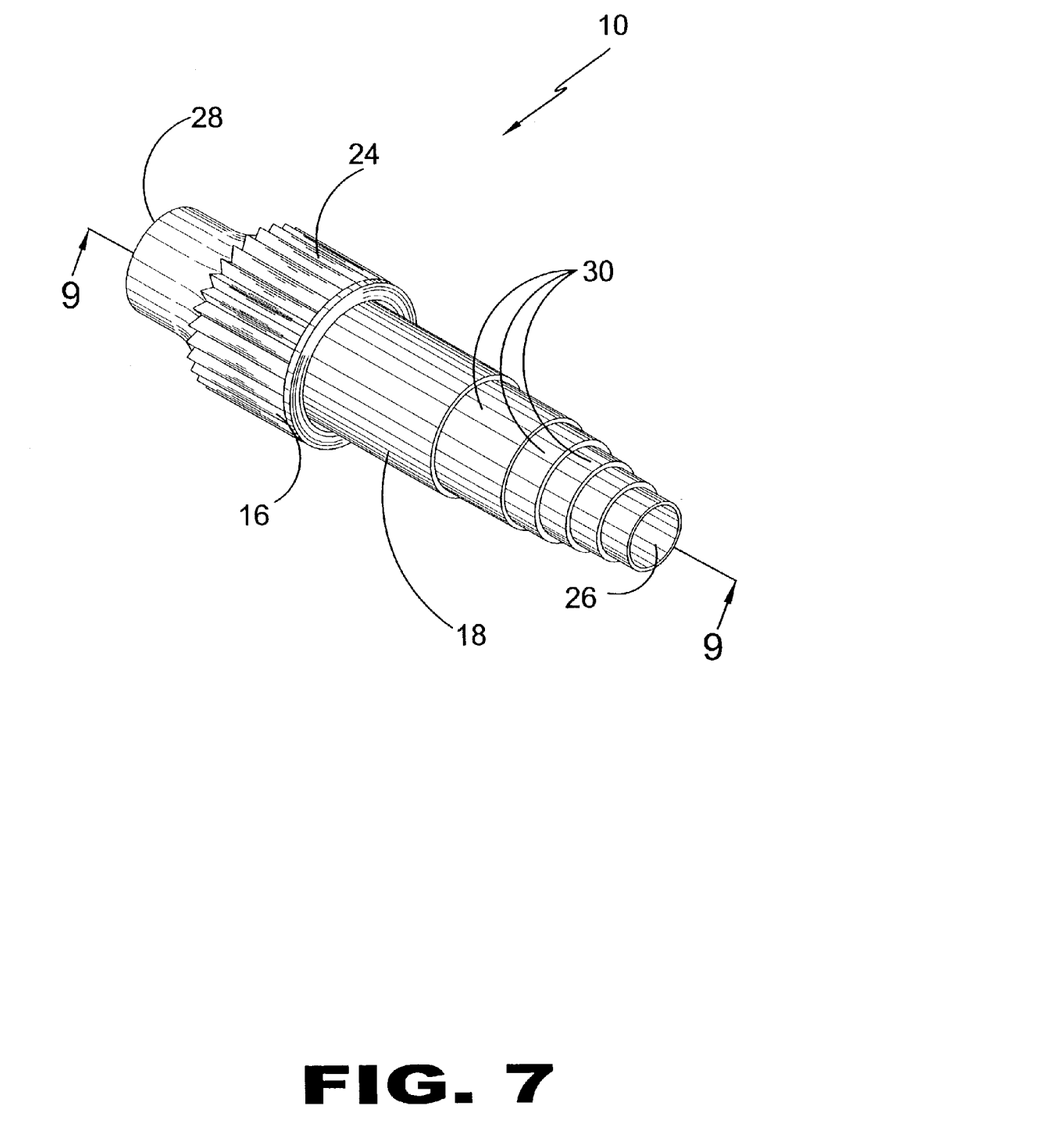
FIG. 7 is a back perspective view of the present invention.

Turning to FIG. 7, shown therein is a back perspective view of the present invention 10. Shown is the rear portion of the present invention 10 depicting the attachment assembly 18 having a radially descending attachment area 30 leading to an inlet 26 that a tube produced of any elastomeric material may be fitted over by stretching or pressing until an adequate liquid tight frictionally maintained connection is produced to provide a flexible urine conduit from the user's implanted catheter to the present invention's selectively rotatable outlet port 28. Also shown is the forward assembly 16 with gripping surface 24.

Figure 8:
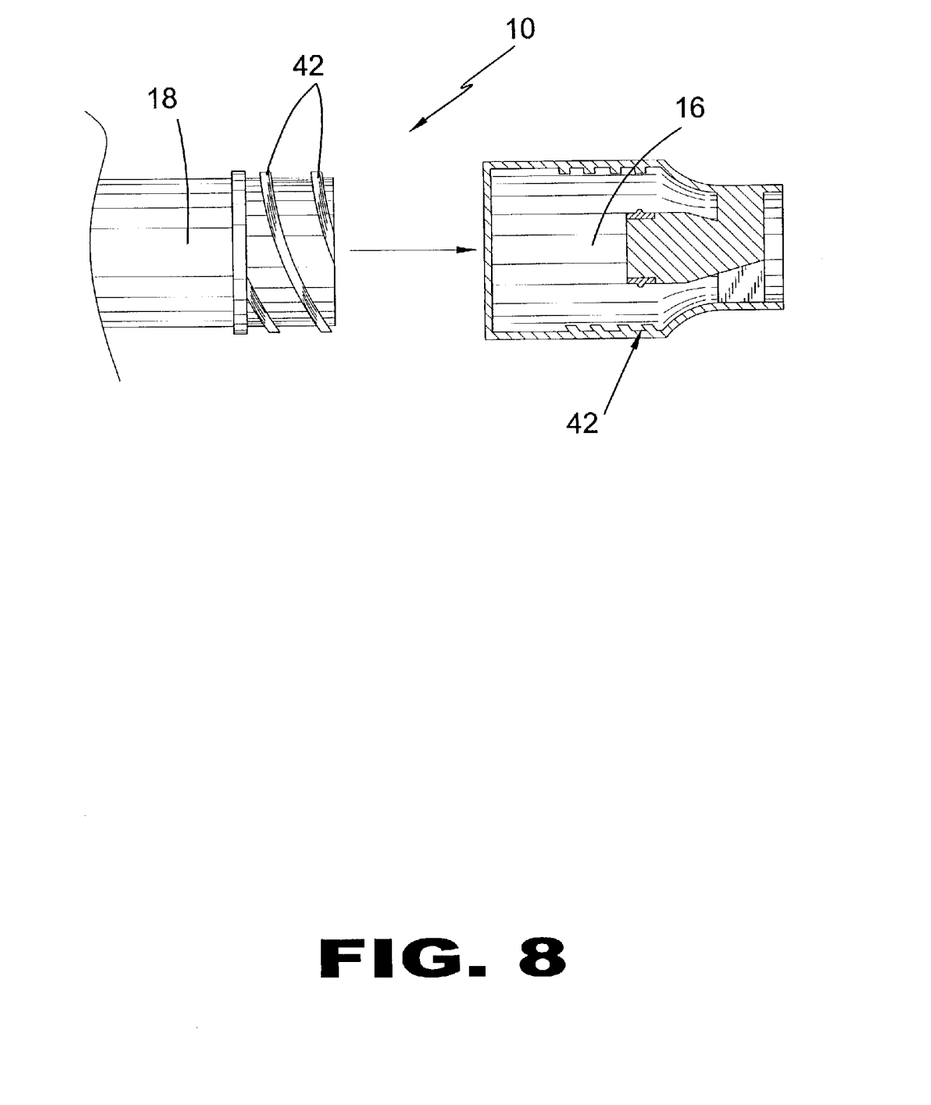
FIG. 8 is an exploded view of the present invention.

Turning to FIG. 8, shown therein is an exploded view of the present invention 10. Shown are the two primary components of the present invention 10, the forward assembly 16 and attachment assembly 18. The forward assembly 16 is pressed onto the attachment assembly 18 within the distal end of the forward assembly. Mating threads 42 of the attachment assembly 18 and forward assembly 16 are also shown.

Figure 9:
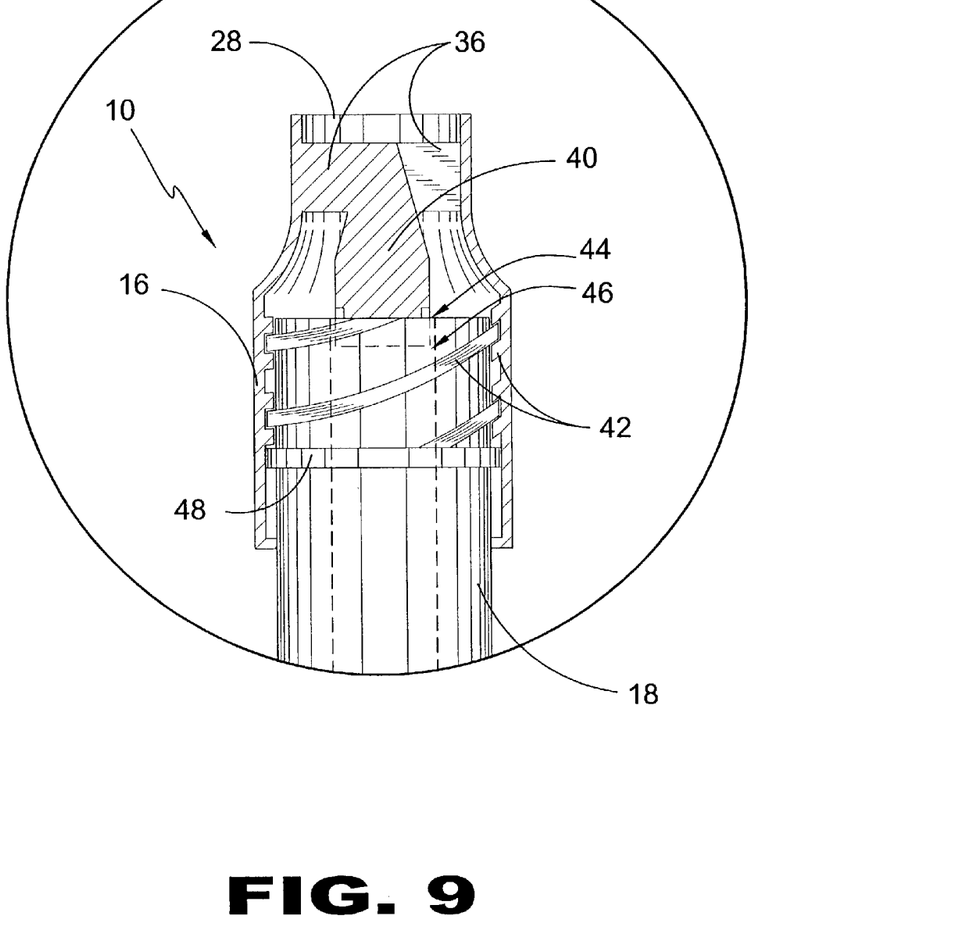
FIG. 9 is a sectional view of the present invention in the closed position.

Turning to FIG. 9, shown therein is a sectional view of the present invention 10 in the closed position. Shown is the present invention 10 in the sealed position depicting the forward assembly 16 in such a position that causes the centerpost 40 to be inserted within the opening or aperture 46 of the attachment assembly 18 to serve as a plug to effectively produce a seal. A gasket 44 positioned between the engaging forward assembly 16 centerpost 40 and attachment assembly 18 aperture 46 and having locking means 42 assures the users that the forward assembly will not randomly rotate causing the valve to leak. Also shown are outlet 28, threads 42 and stop ring 48.

Figure 10:
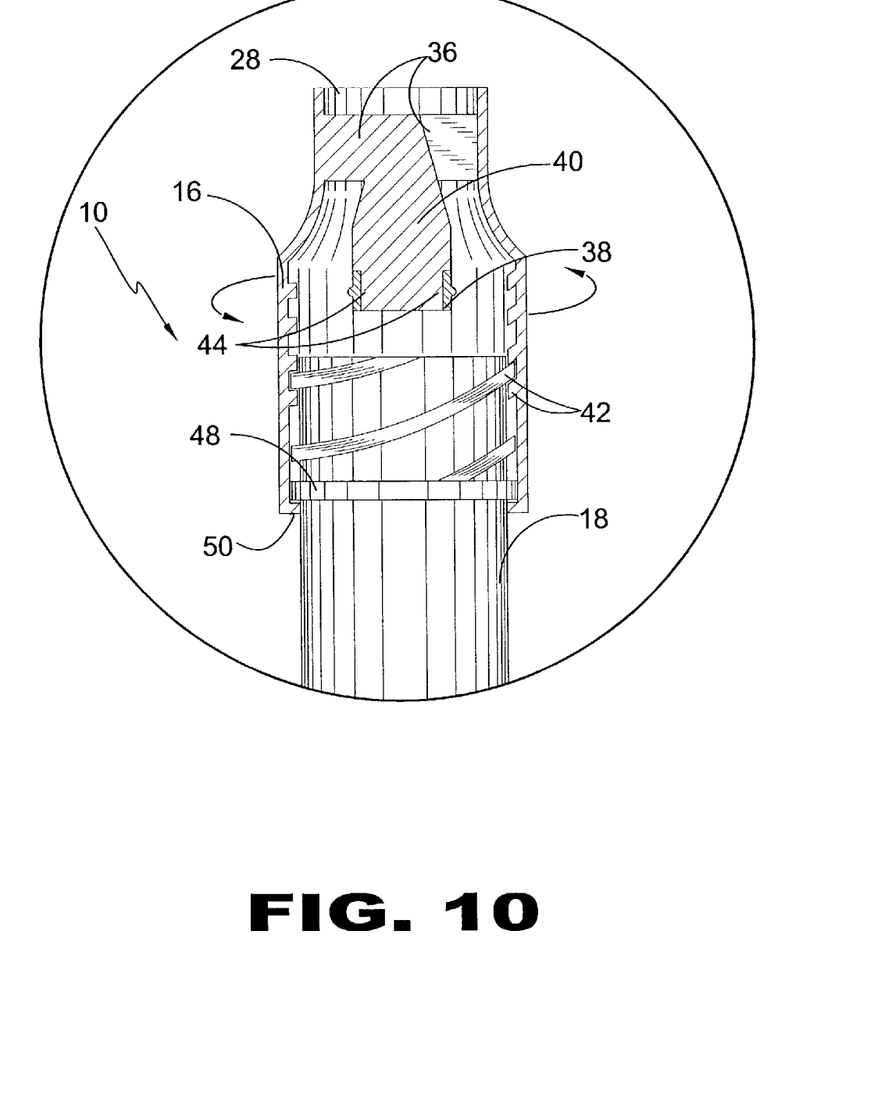
FIG. 10 is a sectional view of the present invention in the open position.

Turning to FIG. 10, shown therein is a sectional view of the present invention 10 in the open position. Shown is the forward assembly 16 in a position that causes the centerpost 40 to be in a dislodged position not providing a seal and releasing any fluid that may be present. The positioning is achieved by rotating the forward assembly 16 forward until a sufficient dislodging advancement or until the stop ring 48 causes advancement to stop by contacting the inwardly disposed flange 50 on the rear end of the forward assembly. Additionally, the stop ring 48 prevents the unintentional unscrewing or removal of the forward assembly 16 from the attachment assembly 18. Also shown are outlet 28, centerpost supports 36, threads 42, and gasket 44 with O-ring like flange element 38.

Figure 11:
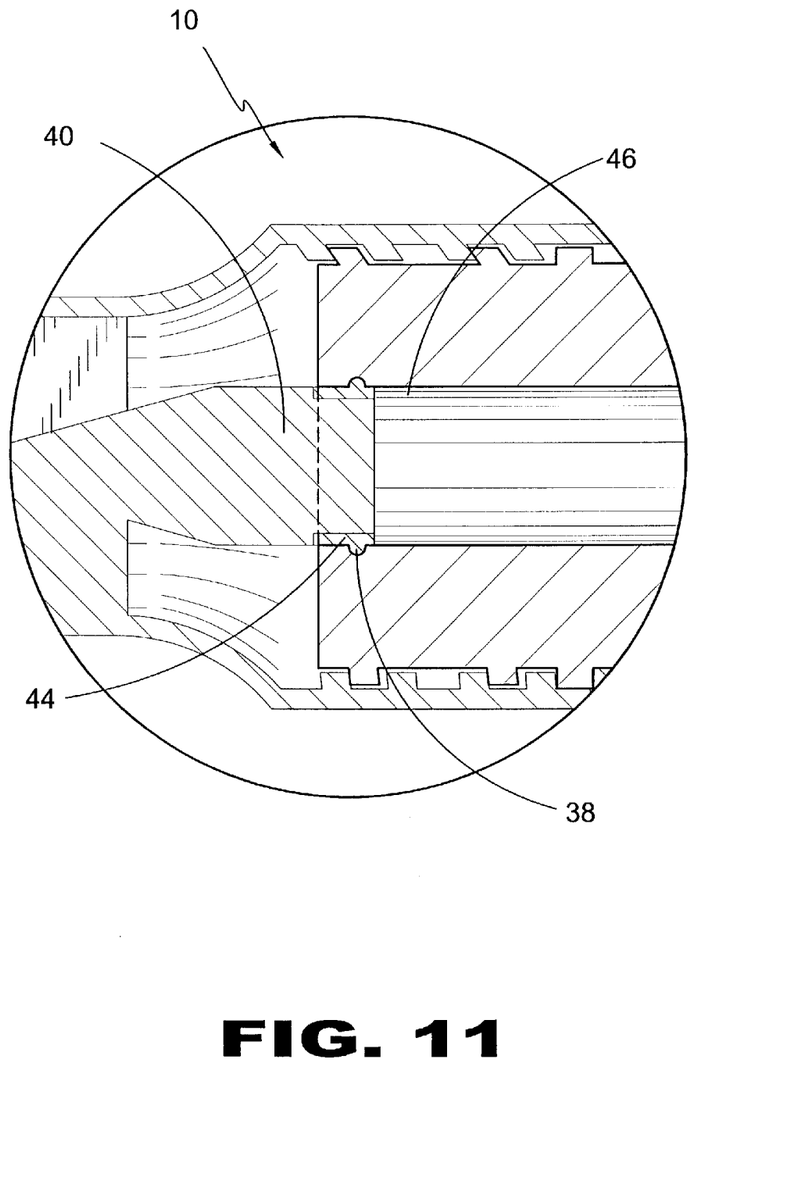
FIG. 11 is a detailed side sectional view of the present invention in the closed position.

Turning to FIG. 11, shown therein is a detailed side sectional view of the present invention 10 in the closed position. Shown is the present invention 10 having a gasket 44 coating the surfaces of the distal end of the center post 40 and interior sides of the attachment assembly aperture 46 to provide a more efficient liquid tight seal to prevent leakage. Additionally a flange or ring 38 may be provided on the gasket 44 to facilitate a locking action to insure a proficient seal being obtained and to present a marginal effort to rotate the forward assemble to prevent the unintentional opening of the valve that may otherwise be caused by vibration or movement of the user's body. The life expectancy of the sealing surfaces is two months. It is recommended that the catheter valve be changed every time the catheter is changed.

Figure 12:
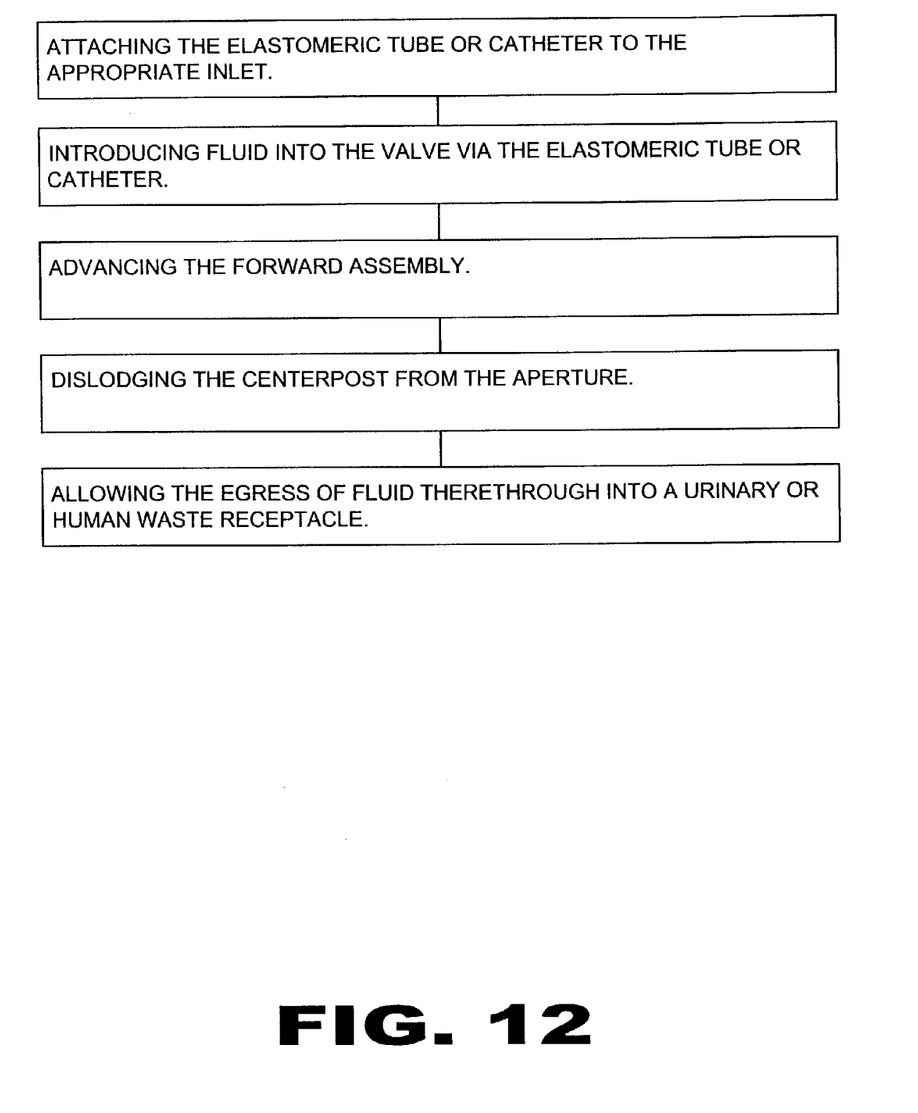
FIG. 12 is a flow chart demonstrating the method of operation of the present invention.

Turning to FIG. 12, shown therein is a flow chart of the method of operation of the present invention. Shown is the method of operation of the present invention. The present invention is a catheter valve that provides for the natural expansion and contraction of the bladder thereby preventing the atrophy thereof. The steps of operation are: 1) attaching the elastomeric tube or catheter to the appropriate inlet; 2) introducing fluid into the present invention via the elastomeric tube or catheter; 3) advancing the forward assembly; 4) dislodging the centerpost from the aperture; and 5) allowing the egress of fluid therethrough into a urinary or human waste receptacle.

What is claimed to be new and desired to be protected by Letters Patent is set forth in the appended claims.

I claim:

1. A valve for placement inline on a catheter to allow a patient to control fluid flow through the catheter, comprising:
   a) a tubular forward assembly having a fluid passageway therethrough, said forward assembly having inner and outer surfaces, and outlet threads on said inner surface on a side of said forward assembly opposite said outlet;
   b) a centerpost centrally disposed in and connected to said forward assembly forming a fluid passageway around the centerpost;
   c) a tubular attachment assembly having a fluid passageway therethrough, said attachment assembly having inner and outer surfaces, wherein said fluid passageway provides a conduit therein, said conduit being centrally disposed and having an inlet therein for receiving fluid from the catheter,
   said conduit for receiving an end of said centerpost on a side opposite said catheter, threads disposed on said outer surface of said inlet for mating rotatable connection with said threads on said forward assembly so that the position of said centerpost can be varied with respect to said conduit to permit control of the flow of fluid through the conduit; and
   d) means for attaching said attachment assembly to the catheter whereby a leak proof attachment is provided for catheters of varying sizes;
   e) a knurled gripping surface disposed on said outer surface of said forward assembly to permit the patient to easily rotate the valve;
   f) a plurality of centerpost supports for connecting said centerpost to said forward assembly, said centerpost supports being radially spaced apart equally about said centerpost and connected between said centerpost and said inner surface of said forward assembly to permit fluid to pass between the supports.

2. The valve of claim 1, wherein said supports are connected to said centerpost and said centerpost mates with said conduit on a side opposite the connection to said supports.

3. The valve of claim 2, wherein said means for attaching said attachment assembly to the catheter comprises a plurality of flanges disposed on an end said attachment assembly, wherein said flanges have a progressively smaller diameter so that one of said flanges will be of a proper size to mate with the catheter, said flanges becoming smaller in diameter extending outward from said attachment assembly.

4. The valve of claim 3, further comprising means for a gasket disposed on said centerpost whereby a leak proof seal is formed between the centerpost and the conduit.

5. The valve of claim 4, wherein said means for a gasket comprises a gasket disposed around said centerpost forming a leak proof seal between said centerpost and said conduit.

6. The valve of claim 5, wherein said gasket is disposed internal said conduit to permit a leak proof seal to form between the centerpost and the conduit when said centerpost is positioned to stop the fluid flow through the conduit.

7. The valve of claim 6, further comprising an O-ring like flange disposed on said outer surface of said gasket to permit a leak proof seal to form between the centerpost and the conduit.

8. The valve of claim 7, further comprising a stop ring disposed internal said forward assembly preventing the forward assembly from being inadvertently removed from the attachment assembly.

9. The valve of claim 8,
   a) wherein said forward assembly has an inwardly disposed flange thereon; and,
   b) said stop ring is disposed internal said forward assembly and inside said flange on said forward assembly, said stop ring having a diameter slightly greater than said flange to prevent said forward assembly from being inadvertently removed from the attachment assembly.

\* \* \* \* \*